(12) United States Patent
Oellermann et al.

(10) Patent No.: US 9,618,499 B2
(45) Date of Patent: Apr. 11, 2017

(54) DIFFUSION CHAMBER FOR ASCERTAINING DIFFERENT PARAMETERS OF AN AQUEOUS SUBSTANCE

(71) Applicant: Alfred-Wegener-Institute Helmholtz-Zentrum fuer Polar- und Meeresforschung, Bremerhaven (DE)

(72) Inventors: Michael Oellermann, Bremen (DE); Felix Christopher Mark, Bremerhaven (DE); Erich Dunker, Schiffdorf (DE)

(73) Assignee: ALFRED-WEGENER-INSTITUT HELMHOLTZ-ZENTRUM FUER POLAR- UND MEERESFORSCHUNG, Bremerhaven (DE)

( * ) Notice: Subject to any disclaimer, the term of this patent is extended or adjusted under 35 U.S.C. 154(b) by 0 days.

(21) Appl. No.: 14/901,745

(22) PCT Filed: Jun. 21, 2014

(86) PCT No.: PCT/DE2014/000322
§ 371 (c)(1),
(2) Date: Dec. 29, 2015

(87) PCT Pub. No.: WO2015/000453
PCT Pub. Date: Jan. 8, 2015

(65) Prior Publication Data
US 2016/0370348 A1    Dec. 22, 2016

(30) Foreign Application Priority Data
Jul. 1, 2013  (DE) ................. 10 2013 011 343

(51) Int. Cl.
*G01N 33/49* (2006.01)
*G01N 21/31* (2006.01)
(Continued)

(52) U.S. Cl.
CPC ............. *G01N 33/4925* (2013.01); *G01J 3/42* (2013.01); *G01N 21/27* (2013.01); *G01N 21/31* (2013.01); *G01N 21/80* (2013.01)

(58) Field of Classification Search
CPC ..... G01N 2021/035; G01N 2021/0353; G01N 2021/0112; G01N 2021/0307;
(Continued)

(56) References Cited

U.S. PATENT DOCUMENTS 3,763,422 A * 10/1973 MacPhee ............. G01N 33/492
  204/400
5,080,865 A *  1/1992 Leiner ...................... G01N 1/28
  204/401

(Continued)

FOREIGN PATENT DOCUMENTS

EP         2110430 B1     10/2009

OTHER PUBLICATIONS

S. Zielinski et al: "Temperature Effects on Hemocyanin Oxygen Binding in an Antarctic Cephalopod", Biol. Bull., vol. 200, Feb. 2001 (Feb. 2001), pp. 67-76, XP002733297.

(Continued)

*Primary Examiner* — Gordon J Stock, Jr.
(74) *Attorney, Agent, or Firm* — Leydig, Voit & Mayer, Ltd.

(57) ABSTRACT

A diffusion chamber for determining different parameters of an aqueous substance includes a vertical central cylinder having a sample chamber for receiving a substance sample and a needle-shaped pH-measuring sensor having a measuring tip which is brought into contact with the substance sample. A spectrophotometer having glass-fiber optics is configured to penetrate the substance sample. A gas supply into the sample chamber is configured to provide a variable gas exposure of the substance sample when determining (Continued)

parameters. A needle of the pH-measuring sensor is inserted into an obliquely extending groove of a slid-in sample slide. A sealing ring on the sample slide is pressed against the central cylinder by means of an inserted spacer ring, the sample chamber is tightly sealed with respect to gases from the surroundings of the diffusion chamber, and a minimum distance is maintained between the lower collimating lens and the substance sample.

13 Claims, 6 Drawing Sheets (51) Int. Cl.
  *G01N 21/27* (2006.01)
  *G01J 3/42* (2006.01)
  *G01N 21/80* (2006.01)

(58) Field of Classification Search
  CPC ..... G01N 2021/1738; G01N 2021/174; G01N 2021/1742; G01N 2021/1744; G01N 21/01; G01N 21/03; G01N 21/0303; G01N 21/17; G01N 21/25; G01N 21/255; G01N 21/27; G01N 21/272; G01N 21/31; G01N 21/75; G01N 21/77; G01N 21/7703; G01N 21/78; G01N 21/783; G01N 21/80; G01N 33/49; G01N 33/4915; G01N 33/492; G01N 33/4925; G01J 3/42; G01J 2003/421
  See application file for complete search history.

(56) References Cited

U.S. PATENT DOCUMENTS

| | | | | |
|---|---|---|---|---|
| 5,128,019 | A * | 7/1992 | Karpf | G01N 21/7703 204/416 |
| 5,242,835 | A * | 9/1993 | Jensen | G01N 21/643 250/458.1 |
| 5,304,492 | A * | 4/1994 | Klinkhammer | G01N 21/643 250/343 |
| 5,335,067 | A * | 8/1994 | Prather | G01N 21/8507 356/436 |
| 5,564,419 | A | 10/1996 | Lundsgaard et al. | |
| 6,009,339 | A * | 12/1999 | Bentsen | G01N 21/05 600/322 |
| 9,080,976 | B2 * | 7/2015 | Hackbarth | G01N 21/6402 |
| 2006/0109469 | A1 | 5/2006 | Schleifer | |
| 2007/0178595 | A1 * | 8/2007 | Raghuraman | G01N 21/80 436/43 |

OTHER PUBLICATIONS

Tan W et al: "Miniaturized fiber-optic chemical sensors with fluorescent dye-doped polymers", Sensors and Actuators B: Chemical: International Journal Devoted to Research and Development of Physical and Chemical Transducers; Elseviers S.A, CH, vol. 28, No. 2, Aug. 1, 1995 (Aug. 1, 1995), pp. 157-163, XP027261054.

* cited by examiner

DIFFUSION CHAMBER FOR ASCERTAINING DIFFERENT PARAMETERS OF AN AQUEOUS SUBSTANCE

CROSS-REFERENCE TO PRIOR APPLICATIONS

This application is a U.S. National Stage Application under 35 U.S.C. §371 of International Application No. PCT/DE2014/000322 filed on Jun. 21, 2014, and claims benefit to German Patent Application No. DE 10 2013 011 343.1 filed on Jul. 1, 2013. The International Application was published in German on Jan. 8, 2015 as WO 2015/000453 A2 under PCT Article 21(2).

FIELD

The invention relates to a diffusion chamber for determining different parameters of an aqueous substance, comprising a vertical central cylinder having at least one sample chamber for receiving a substance sample, a needle-shaped pH-measuring sensor having a measuring tip which comes into contact with the substance sample, a spectrophotometer having glass-fibre optics which penetrate the substance sample, and a gas supply into the sample chamber for variable gas exposure of the substance sample when determining parameters.

BACKGROUND

The pH is a measurement of the acidic or alkaline nature of an aqueous substance. Said substance can exhibit greatly varying properties depending on the current pH thereof. For example, in the case of blood, the pH affects the oxygen-binding properties of blood pigments, such as haemoglobin or haemocyanin. The lower the pH, the less oxygen the blood pigment can bind via the prosthetic group thereof (i.e. iron or copper). This property makes it easier to release oxygen in the tissue when the pH of the blood there lowers due to metabolic release of carbon dioxide (the Bohr effect). If, conversely, carbon dioxide is exhaled via the lungs, the pH of the blood there rises and thus the ability of the blood pigment to absorb oxygen increases. Changes in pH influence the oxygen-binding curves which show the relationship between the prevailing oxygen partial pressure and the percentage of oxygen which is bound to the blood pigment (blood pigment saturation). The oxygen gradient as a decrease in the oxygen partial pressures between the ambient air and the cells of the body determines the absorption of oxygen. Optimal oxygen absorption and release allows efficient oxygen transport and thus makes it possible for the organism to perform very efficiently. Oxygen-rich blood changes shade owing to changes in the conformation of each prosthetic group when binding oxygen. For example, oxygenated haemoglobin exhibits a brighter and more vibrant shade than deoxygenated haemoglobin, whereas oxygenated haemocyanin turns blue. This leads to a change in the absorption behaviour of the substance sample when it is irradiated with ultraviolet or visible light. By simultaneously measuring the pH and the absorption behaviour to determine the oxygen-binding properties of blood in the case of in vivo or almost in vivo studies, important information relating to the current state of the substance or the carrier thereof can thus be obtained. In this case, however, it is also important in particular to be able to manage with only small sample volumes of the substance to be studied, since the amount of the sample material is often very limited (for example in the case of minute organisms).

U.S. Pat. No. 5,564,419 A discloses a device for determining photometrically in vitro the oxygen content in a blood sample. By means of a syringe-type device, the blood can be drawn directly out of the organism and conducted via a channel. Said channel is passed through by openings in a carrier, through which openings light is shone to measure absorption. The openings are sealed with a sealing ring. However, a pH measurement is not carried out. EP 2 110 430 B1 discloses a measuring cell for measuring the biochemical oxygen demand, in which cell the end of a fibre-optic cable from a spectrophotometer is brought into contact with the substance to be studied via a sealing element. U.S. Pat. No. 5,056,520 discloses a needle-shaped optical measuring sensor comprising a fibre-optic cable made from silicon, by means of which sensor the pH of a blood sample can be determined. The fibre-optic cable is guided by a sleeve and the measuring tip thereof ends in a drop of the substance to be studied.

The publication "Method for Continuous Registration of $O_2$-Binding Curves of hemoproteins by Means of a Diffusion Chamber" by H. Sick and K. Gersonde (in Analytical Biochemistry 32, 362-376 (1969) discloses a diffusion chamber for photometrically measuring the absorption behaviour of blood under various gas exposures. In a central cylinder, the blood sample to be studied is placed on an acrylic glass slide and is irradiated with light from a mercury vapour lamp which is detected in a photodetector. The acrylic glass slide is sealed with respect to the central cylinder by a sealing ring. The gas mixtures are introduced into the central cylinder via a gas supply. A pH measurement is not carried out.

The publication "Oxygen evolution in a hypersaline crust: in situ photosynthesis quantification by microelectrode profiling and use of planar optode spots in incubation chambers" by J. Woelfel et al. (in Aquat Microb Ecol Vol. 56:263-273, 2009) discloses using an oxygen microoptode comprising sensor spots and fibre optics for optically measuring the primary production of oxygen in the Arctic. In this case, the oxygen generation of ground-dwelling diatoms outdoors in a benthic chamber is detected online via optical fibres. The basic principle of optical oxygen measurement is based on exciting a specific fluorescent dye (indicator molecule) using light of a defined wavelength and quenching said dye according to the oxygen concentration; see URL cited Jun. 20, 2013 http://www.angewandteoekologie.uni-rostock.de/en/forschung3/analytik0/mikroopt/.

The publication "Temperature Effects on Hemocyanin Oxygen Binding in an Antartic Cephalopod" by S. Zielinski et al. (in Biol. Bull. 200:67-76 (February 2001) describes a diffusion chamber which comprises a modified quartz glass cuvette for simultaneously determining changes in pH and absorption of blood of a cephalopod under in vitro conditions. When it is added to the cuvette, the blood to be studied (400 μl) is distributed to an upper and lower reservoir, which is continuously mixed by means of magnetic stirrers. In a region between the two reservoirs, the blood additionally disperses into a thin layer (0.45 mm) in which the absorption measurement takes place. The measuring tip of a micro pH electrode is introduced into the blood sample via an upper sealing cover to measure the pH. A second opening in the cover makes it possible to expose the sample to a gas mixture which can be varied during the measurement (oxygen, carbon dioxide, nitrogen). The change in absorption which occurs is measured using a spectrophotometer comprising glass-fibre optics. The precise construction is not shown in greater detail in the publication; see FIG. 1 and the paragraph "Analysis of oxygen binding".

However, the measuring procedure is described in detail. The analysis of the oxygen saturation and binding properties of blood pigments by measuring light absorption is predominantly carried out using blood samples which have been buffered to stabilise the pH. Buffers are aqueous solutions of a weak acid and the conjugated base thereof. When adding acidic (having $H_3O^+$ ions) and alkaline solutions (OH), the hydronium ions of the buffer base and the hydroxide ions of the buffer acid are quenched (buffered) so that the pH changes only a little during said addition. However, a buffer is only effective if relatively large amounts of buffer acid and buffer base are present. However, the buffering has a demonstrable effect on the binding properties of the blood pigment and thus does not always accurately reflect the actual physiological properties. In the case of Pörtner (1990 ("An analysis of the effects of pH on oxygen binding by squid (lllex illecebrosus, *Loligo pealei*) haemocyanin", J. Exp. Biol. 150, 407), 1994 ("Coordination of metabolism, acid-base regulation and haemocyanin function in cephalopods", Mar. Fresh. Behav. Physiol. 25, 131-148)) and Zielinski et al. (2001, "Temperature effects on hemocyanin oxygen binding in an Antarctic cephalopod", Biol. Bull. (Woods Hole) 200, 67-76), this problem is solved in that native, unbuffered blood was studied at a constant oxygen partial pressure, but with a varied pH. By measuring additional binding curves at various oxygen partial pressures, the same parameters could thus be determined as in the case of conventional methods having the above-mentioned disadvantages. However, in the case of the method of Pörtner and Zielinski et al., the inventors have recognized that it is disadvantageous that high sample consumption occurs and the pH measurements are carried out on pooled blood samples, and therefore the measurements cannot be clearly attributed to individual organisms and also cannot be statistically evaluated.

SUMMARY

In an embodiment, the present invention provides a diffusion chamber for determining different parameters of an aqueous substance. The diffusion chamber includes a vertical central cylinder having at least one sample chamber for receiving a substance sample and a needle-shaped pH-measuring sensor having a measuring tip configured to be brought into contact with the substance sample. A spectrophotometer having glass-fibre optics is configured to penetrate the substance sample. A gas supply into the sample chamber is configured to provide a variable gas exposure of the substance sample when determining parameters. A sample slide is slid radially into the central cylinder in a gas-tight manner, the central cylinder having a cylindrical opening, above which a cylindrical sealing ring surrounding the sample chamber is disposed on the sample slide. A needle of the pH-measuring sensor which is in the form of a syringe-type optical microsensor is inserted into an obliquely extending groove of the sample slide. A glass fibre bearing the measuring tip is movably mounted in the needle, and the needle is guided through the sealing ring in a gas-tight manner. An upper cylindrical lens holder comprising a light-supplying glass fibre and an upper collimating lens is slid axially into the central cylinder in a gas-tight manner above the sample chamber, and a lower cylindrical lens holder comprising a light-diverting glass fibre, a lower collimating lens and a spacer ring is slid axially into the central cylinder in a gas-tight manner below the sample chamber. The sealing ring on the sample slide is pressed against the central cylinder by the inserted spacer ring, the sample chamber is tightly sealed with respect to gases from the surroundings of the diffusion chamber, and a minimum distance is maintained between the lower collimating lens and the substance sample.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In an embodiment, the present invention provides a diffusion chamber in which both pH and absorption measurements can be carried out simultaneously and on very small substance samples. In this case, the measurements are to proceed as quickly as possible and provide high-resolution measurement results at the same time.

The diffusion chamber according to an embodiment of the invention is characterised in that a sample slide is slid radially into the central cylinder in a gas-tight manner, which cylinder has a cylindrical opening. Above the cylindrical opening, a cylindrical sealing ring surrounding the sample chamber is arranged on the sample slide. Into an obliquely extending groove in the sample slide, a needle of a syringe-type optical microsensor is inserted according to an embodiment of the invention. Said microsensor forms the pH-measuring sensor. In this case, a glass fibre bearing the measuring tip is displaceably mounted in the needle. Moreover, the needle is guided through the sealing ring in a gas-tight manner. Furthermore, the diffusion chamber according to an embodiment of the invention is characterised in that an upper cylindrical lens holder comprising a light-supplying glass fibre and an upper collimating lens is slid axially into the central cylinder above the sample chamber, and a lower cylindrical lens holder comprising a light-diverting glass fibre, a lower collimating lens and a spacer ring is slid axially into said central cylinder below the sample chamber. In this case, according to an embodiment of the invention, by means of the inserted spacer ring, the minimum light path from the collimating lens to the sample is maintained, the sealing ring on the sample slide is pressed against the central cylinder, and the sample chamber is tightly sealed with respect to gases from the surroundings of the diffusion chamber.

In the case of the diffusion chamber according to an embodiment of the invention, firstly in the case of a diffusion chamber, an optical microsensor—what is known as a "pH optode"—is used to measure the pH, by means of which the measurements are determined optically with a good measuring frequency and high measuring accuracy. All known diffusion chambers up to now have measured the pH externally in a blood sample which is exposed to gas in parallel, electrically using pH electrodes which have relatively large space requirements and, as a result of the relatively large sensor diameter, also require a relatively large sample volume. A further advantage of the pH optode consists in the fact that it is possible to carry out measurements in a stable, accurate and fast manner over a wide range of temperatures (including 0° C. and colder). By contrast, conventional pH electrodes can only carry out measurements in cold environments in an extremely slow and unstable manner. The pH optode used in an embodiment of the invention is constructed in the manner of a syringe and has a needle in which a glass fibre is displaceably mounted. The free end of the glass fibre bears the measuring tip and can have a diameter of 150 µm or less. The measuring volume of the substance sample can be correspondingly small, it can be 20 µl or less. For example, 10-15 µl is sufficient for the substance sample—by contrast, up to now in the prior art, 400 µl to 3 ml was required.

A particular challenge in the case of the diffusion chamber according to an embodiment of the invention is integrating a pH optode of this type into the measuring arrangement. For this purpose, in the case of an embodiment of the invention, a special sample slide is provided which has an oblique groove. The groove extends from the body of the needle obliquely, ascending to the end of the needle. In this way, it is ensured that the measuring tip of the glass fibre which is slid out of the needle is immersed in the substance sample and does not extend beyond it. During the measurements, the substance sample is exposed in a targeted manner to gas mixtures of a known composition (partial pressure). In this case, it must be ensured that ambient air does not inadvertently enter the gas stream or come into direct contact with the substance sample. For this purpose, in the case of the diffusion chamber according to an embodiment of the invention, it is provided that a sealing ring is arranged on the sample slide, through which ring the needle is guided in a gas-tight manner. The sealing ring surrounds the sample chamber, which is formed above an opening in the sample slide. The substance sample to be studied is applied to a glass plate which is positioned over the opening under the sealing ring. In this way, the light beam of the spectrophotometer can irradiate the substance sample and measure the absorption thereof.

Another challenge in the case of the diffusion chamber according to an embodiment of the invention is integrating the fibre optics of the spectrometer into the measuring arrangement. This has been solved according to an embodiment of the invention by two cylindrical lens holders which are arranged above and below the sample chamber. The two lens holders fix the glass fibres from the light source (above) and to the spectrophotometer (below) and support the convergent lenses and a plurality of sealing rings. They can easily be slid or screwed into the central cylinder and thus sealed. A spacer ring is additionally arranged on the lower lens holder. When inserted, said ring presses against the slid-in sample slide from below and ensures a minimum distance from the convergent lens to the substance sample. The sample slide in turn presses the sealing ring arranged thereon against the inside of the central cylinder and thus brings about a sealing of the sealing ring in the central cylinder. This prevents ambient air, which would distort the measurements, from flowing into the sample chamber during the measuring process.

As a result of being able to use a compact, high-resolution pH optode and a compact, high-resolution spectrophotometer due to the special integration of the respective fibre optics, by means of the diffusion chamber according to an embodiment of the invention, a very compact, transportable and efficient measuring apparatus can be provided, by which even the smallest substance sample volumes, for example small amounts of blood from very small organisms, can be measured reliably and accurately in high resolution. In this case, the measurements can be determined on identical substance samples at the same time, so that by means of this consistency, the representativity of the measurement results can be further increased and the range of applications can be broadened.

It has already been noted further above that it is essential for the measuring tip to end up in the substance sample. For this purpose, the needle of the pH optode is inserted obliquely into the sample slide. For this purpose, said slide comprises an oblique groove. In order to further improve the immersion of the measuring tip at the end of the glass fibre in the substance sample, it is advantageous and preferable for the needle to have two angular bends so that the end of the needle which is open for sliding out the glass fibre is shifted in parallel. The needle is thus lifted to a level in the middle of the substance to be studied. The glass fibre thus only needs to be slid out of the needle to a small degree and cannot lower any further. The substance sample is irradiated with light to measure absorption. In this case, it must be ensured that no foreign bodies, which would absorb the light and lead to measurement errors, enter the light beam. Such errors in the absorption measurement can preferably and advantageously be prevented in the diffusion chamber according to an embodiment of the invention by ensuring that the end of the needle which is open for sliding out the glass fibre sits flush with the inner contour of the sealing ring, and the measuring tip of the glass fibre which is slid out of the needle is immersed in an edge region of the substance sample to be studied. Neither the needle nor the slid-out glass fibre thus adversely affects the incident light beam. So that this remains safely ensured during the measurements, it is preferable and advantageous for the optical microsensor to be fixed in the sample slide by means of an oblique screw connection in a straight groove. After the insertion, the easily accessible screw connection can be actuated and the optical microsensor or the syringe body thereof can be fixed. Furthermore, in order to ensure reliable measurement results, it is preferable and advantageous for the measuring tip to have a diameter of less than 150 µm. As a result, very small substance sample volumes can be used. The reliable immersion of the particularly small measuring tip is nevertheless safely ensured. In addition, neither the small measuring tip nor the glass fibre bearing said tip absorb light to such an extent that the measurement results could be distorted.

As a result of being able to use very small substance sample volumes in the diffusion chamber according to an embodiment of the invention, a measurement volume of less than 20 µl can preferably and advantageously be used in the sample chamber for the substance sample to be studied.

Thus for example more measurements can be carried out per blood sample, or blood samples from even the smallest organisms can be studied using limited amounts of blood. Furthermore, measurement profiles, for example determining pH gradients by means of the change in the other measurement parameters, for example variations in the gas composition, temperature, excitation and detection wavelength, can also be created, when the optical microsensor preferably and advantageously has a measurement control for determining at least one measurement per second. Likewise, it is particularly advantageous and preferable when creating accurate measurement profiles for the spectrophotometer to have a measurement control for determining at least 1000 spectra per second in a continuous wavelength range of between 200 nm and 1100 nm. In this case, each spectrum can be converted into for example 2048 data points. This high data density provides many details about the entire spectrum, which is advantageous for example in the case of non-model organisms or abnormal blood samples. Such spectrophotometers and pH optodes are commercially available; see embodiments. By means of efficient measuring devices of this type, which are flexible and compact and therefore also allow field experiments, the data density is considerably increased for example per binding curve determined. For example, in a two-hour measuring period, 7,200 data points can be determined in only a short integration time. In known methods, by contrast, generally only 6 to 20 data points can be determined. Such a high recording rate can be used firstly to considerably reduce the instrumental noise by means of averaging. Secondly, almost continuous binding curves can be determined, by means of which new, partially parametrically very narrowly limited binding properties can be revealed. An example of this is the curve asymmetry of the binding curves as a function of the oxygen partial pressure.

Further above, it has already been noted that in the case of the diffusion chamber according to an embodiment of the invention, the flexibility with respect to the measurement parameters is advantageous. As a result of the particular construction thereof, an embodiment of the invention allows the use of special high-resolution, fibre-based pH optodes and spectrophotometers. In particular, it is also advantageous and preferable for the spectrophotometer to have a halogen or luminescence light source for irradiating the substance sample to be studied. As a result, by means of the diffusion chamber according to an embodiment of the invention, colorimetric assays or fluorescence or luminescence assays can also be created. This applies for example for cell suspensions in which for example the NADH activity, calcium activity and ATP activity, oxygen-radical activity or caspase activity is to be measured, while simultaneously measuring the pH and cellular or physiologically relevant gas composition. For fluorescence measurements, only an LED light source which emits light in a single defined wavelength, has to be connected to the optical fibre system of the spectrophotometer via a Y-wave guide. It is not necessary to replace the spectrophotometer. Furthermore, the sample chamber can advantageously and preferably be supplied with an adjustable gas mixture, for example of nitrogen, oxygen and carbon dioxide, via the gas supply, in order to allow the above-mentioned parameter variation of the environment of the substance sample to be studied.

The flexibility of the diffusion chamber according to an embodiment of the invention with respect to the applicability thereof to different measuring problems can be improved yet further if additional measuring tips of additional optical microsensors, for example for measuring the $O_2$, $CO_2$ or NO content, or of chemical microsensors, for example for detecting colour-sensitive compounds, are preferably and advantageously introduced into the sample chamber of the substance sample to be studied. As a result of the availability of $O_2$, $CO_2$ or NO optodes which are available on the market and can be readily integrated into the construction of the diffusion chamber according to an embodiment of the invention, further parameters in addition to the pH can be determined ($O_2$, $CO_2$ or NO content). As a result, the range of possible uses of the diffusion chamber according to an embodiment of the invention can be further expanded. In addition, it is possible to link for example chemical measurements, in which for example colour-sensitive compounds are measured, to the simultaneous pH measurement by the diffusion chamber according to an embodiment of the invention. For the substance sample to be studied, preferably and advantageously a substance of biological origin, for example blood or a cell suspension, it is advantageous and preferable for the sample chamber or the housing which surrounds the sample chamber to be tempered with distilled water or water supplemented with glycol. Further advantageous modifications and explanations relating to the above-mentioned embodiments of the diffusion chamber according to embodiments of the invention can be found in the embodiments described below.

Figure 1:
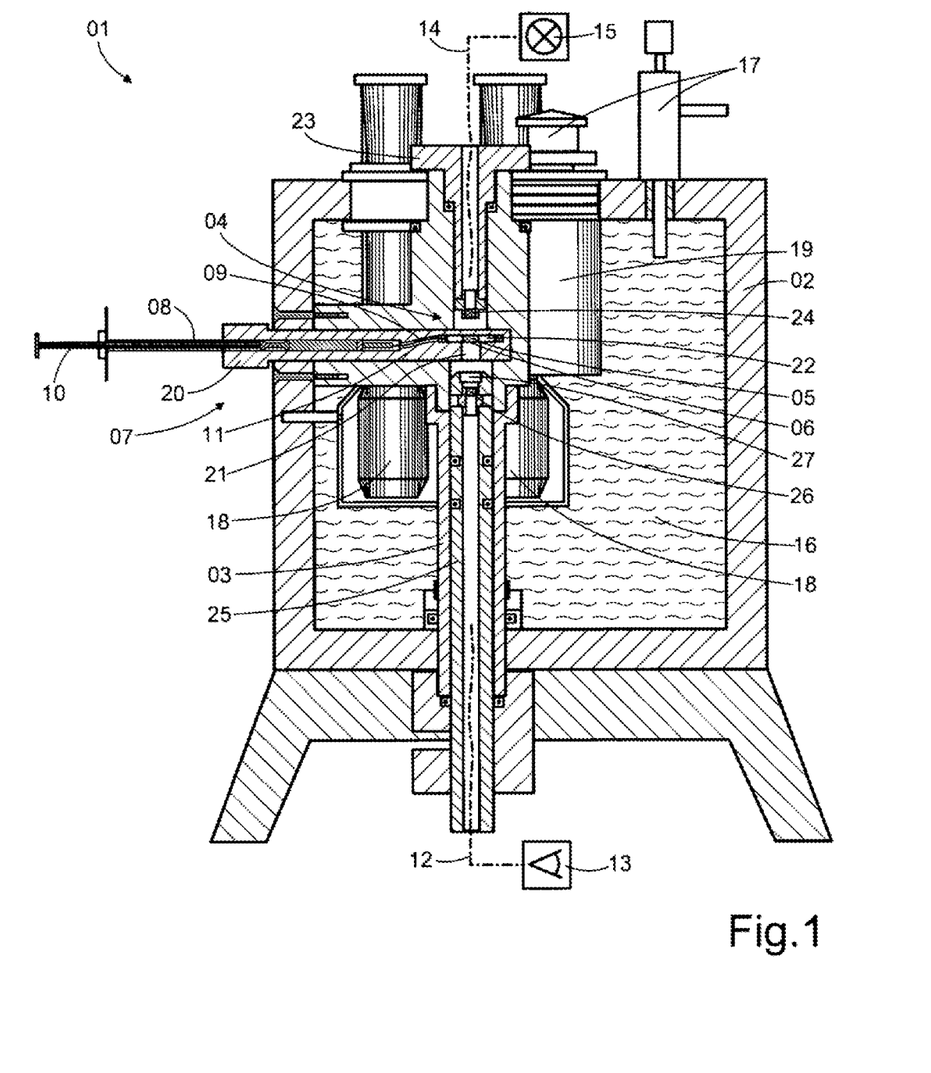
FIG. 1 is a schematic, cross-sectional view of an embodiment of the diffusion chamber.

FIG. 1 shows the diffusion chamber 01 according to an embodiment of the invention in a schematic, cross-sectional view. A vertical central cylinder 03 is located in a housing 02, in the central region of which cylinder a sample chamber 04 is arranged for receiving an aqueous substance sample 05. The substance sample 05 is applied thinly to a glass plate 06 (rectangular haematocrit plate, relatively thick cover slip). An optical microsensor 07 (pH optode) having a syringe body 08, a plunger 10 and a needle 11 is arranged on the left-hand side of the housing 02, into which needle a glass fibre 09 is guided. In the lower region of the housing 02, a glass fibre 12 extends centrally in the central cylinder 03, which fibre leads to a spectrophotometer 13. In the upper region of the housing 02, a glass fibre 14 extends centrally in the central cylinder 03, which fibre leads to a light source 15.

The housing 02 is filled with a water reservoir 16, the temperature of which is kept constant by means of a thermostat. A gas inlet distributor 17 (for connecting a plurality of lines for different gas mixtures) is arranged on top of the housing 02. From there, the supplied gas mixture at any given time, which is premixed to the desired gas ratios by means of a gas-mixing pump, and introduced steadily and in a uniform gas flow throughout the entire measurement cycle, is conducted to gas humidifiers 18 via the tempered water reservoir 16. In this case, it is a glass cylinder in which the supplied dry gas mixture is saturated with water and equilibrated to the measuring temperature. As a result, the substance sample is not dried out and also does not change the measuring temperature thereof during the gas exposure. In the gas humidifiers 18, the gas mixture is driven through a porous membrane, over which a small water column rests. This results in fine gas bubbles which quickly become saturated with water vapour. From the gas humidifiers 18, the damp gas mixture flows into a gas distributor 19, which then conducts the gas mixture continuously into the sample chamber 04 and over the substance sample 05.

A sample slide 20 is slid radially into the central cylinder 03 in a gas-tight manner, which cylinder has a cylindrical opening 21. Above said opening, a cylindrical sealing ring 22 is arranged, which surrounds the sample chamber 04 in a gas-tight manner. Further details can be found in FIGS. 2 and 3. An upper cylindrical lens holder 23 comprising the light-supplying glass fibre 14 and an upper collimating lens 24 is slid axially into the central cylinder 03 above the sample chamber 04, and a lower cylindrical lens holder 25 comprising the light-diverting glass fibre 12, a lower collimating lens 26 and a spacer ring 27 is slid axially into said central cylinder below the sample chamber 04. It should be noted that the inserted spacer ring 27 presses the sample slide 20 and the sealing ring 22 arranged thereon against the inner contour of the central cylinder 03 and as a result protects the sample chamber 04 during the measurements against the penetration of ambient air, which would distort the measurements. Further details can be found in FIGS. 4 and 5.

A possible measurement cycle by the diffusion chamber 01 is as follows:

15 µl substance sample 05 (for example blood) are applied to the glass plate 06 of the sample slide 20 and then slid into the sample chamber 04.

the substance sample 05 is then exposed to a 100% $O_2$ gas stream, until the absorption of the substance sample 05 no longer changes (=100% calibration)

the $O_2$ gas stream is then adjusted steadily to for example 21 kPa (partial pressure $PO_2$ during the measurement cycle) and maintained until the absorption of the substance sample 05 is stable again and no longer changes.

a $CO_2$ gas stream is then increased incrementally (or continuously), in order to lower the pH of the substance sample 05 to such an extent that the absorption of the substance sample 05 does not decrease any further ($CO_2$ dissolves in the substance sample 05 and, by forming carbonic acid, leads to a decrease in the pH), it is then exposed to a 100% $N_2$ gas stream in order to determine the 0% calibration value (the absorption of the substance sample 05)

throughout the entire measurement cycle, the measurement of the pH (by the pH optode 07) and of the absorption of the substance sample 05 (by the spectrophotometer 13) is carried out with the greatest possible measurement frequency in order to be able to determine the highest-possible resolution and thus particularly representative oxygen-binding curves from the data sets obtained.

Figure 2:
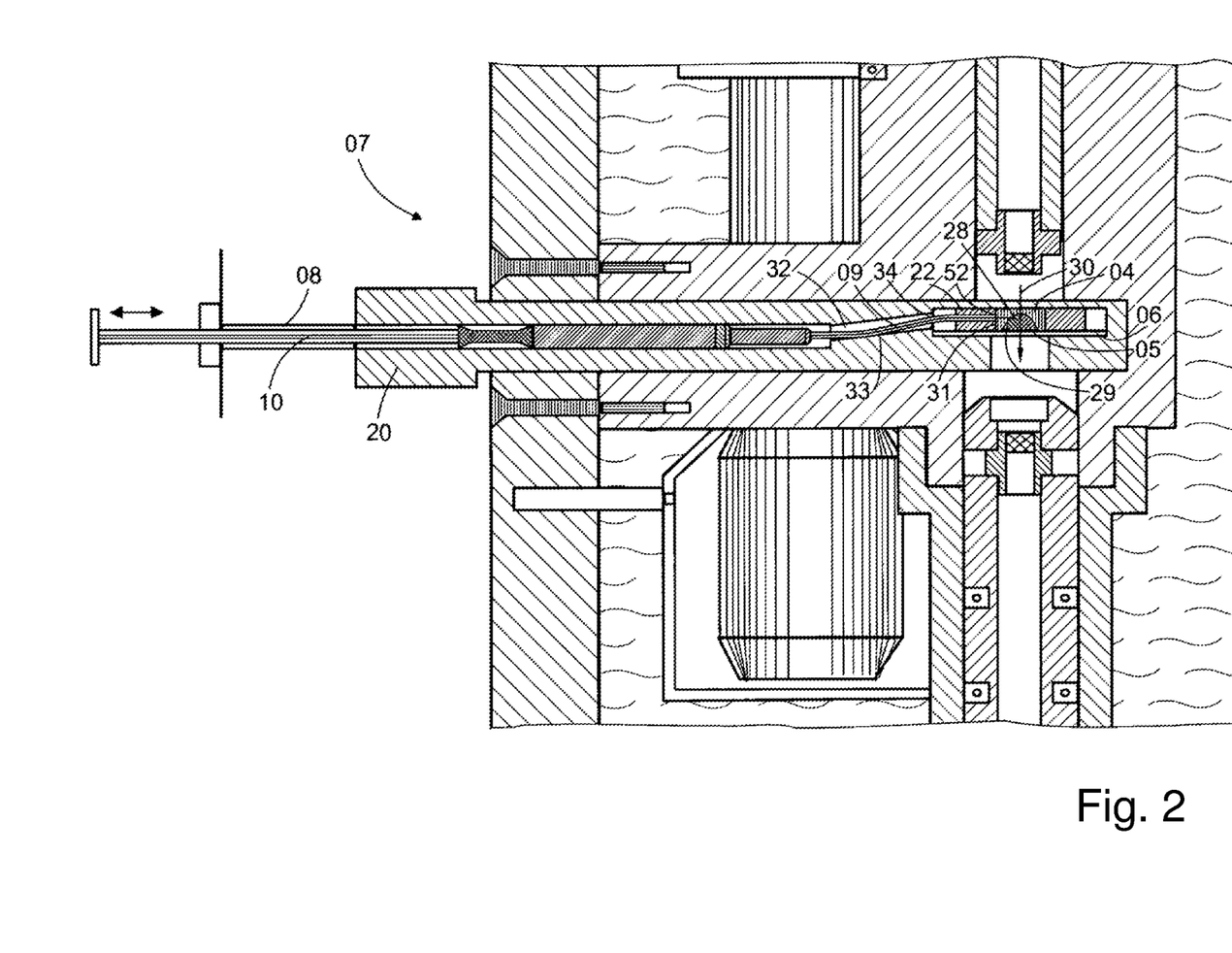
FIG. 2 is a detail from the embodiment of the diffusion chamber.

FIG. 2 shows the sample slide 20 having the pH optode 07 in detail. The syringe body 08, the plunger 10 and the needle 11 can be seen. The optical glass fibre 09 is guided in the needle 11. Said fibre bears a measuring tip 28, which is coated for example with an indicator molecule (see the introduction to the description). By moving (double arrow) the plunger 10, the glass fibre 09 and thus the measuring tip 28 is shifted radially and slid out of the open end 52 of the needle 11. As a result, the measuring tip 28 ends up in an edge region 29 of the substance sample 05 and does not disrupt the optical path 30 to the absorption measurement. The needle 11 is slid through the sealing ring 22 in a gas-tight manner and sits flush with the inner contour 31 of the sealing ring 22. The optical path 29 is thus not disrupted by the needle 11 either. In FIG. 2, it can also be seen that the sample slide 20 has a groove 32 which extends obliquely, ascending to the sample chamber 04. As a result, and due to the two angular bends 33, 34 of the needle 11, it is ensured that the measuring tip 28 is also reliably immersed in the edge region 29 of the substance sample 05 and does not protrude beyond it.

As a pH optode 07, for example the commercially available glass-fibre-based pH microsensor by the company PRESENSE GMBH can be replaced with a very small measuring tip 28 (150 µm); see www.presens.de/products/brochures/category/sensor-probes/brochure/ph-microsensors.html, cited Jun. 23, 2013. This pH optode is temperature-stable and, with one measurement per second, also very fast. As a spectrophotometer 13, for example the commercially available glass-fibre-based spectrophotometer by the company OCEANOPTICS can be used; see http://www.oceanoptics.com/products/usb2000+.asp, cited Jun. 23, 2013. Said spectrophotometer in combination with a deuterium and halogen light source 15 (DT-Mini-2-GS, Ocean-Optics) records a wide, continuous spectrum (200-1100 nm) with a resolution of 2048 data points per spectrum. This high data density provides many details about the entire spectrum. Furthermore, the spectrophotometer can record up to 1000 spectra per second. Together with the likewise high amount of data owing to the pH optode, the amount of data is considerably increased in comparison with known diffusion chambers.

Figure 3:
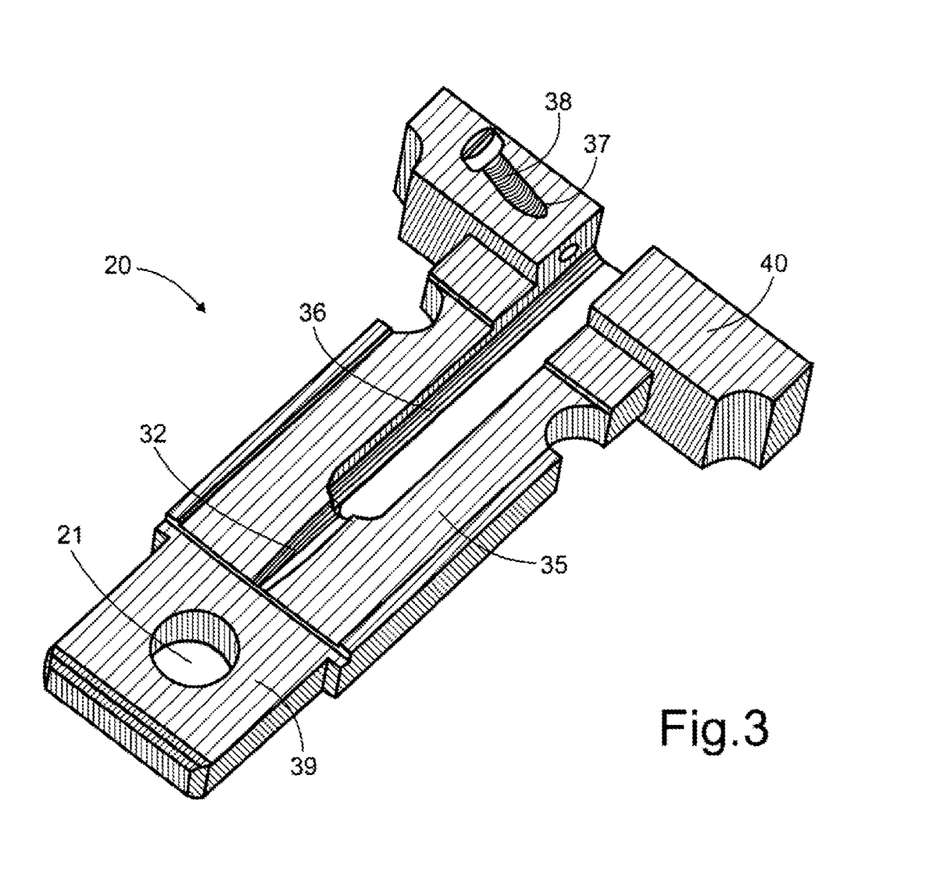
FIG. 3 is a detailed view of an embodiment of the sample slide.

FIG. 3 shows the sample slide 22 in detail. A slide body 35 can be seen, into which the oblique groove 32 is milled. A straight groove 36 is provided for the insertion of the syringe body 08. Furthermore, an oblique hole 37 is provided for an oblique screw connection 38 of the syringe body 08 when inserted. In the front region, the slide body 35 bears a rectangular supporting surface 39 for resting the glass plate 06 with the substance sample 05. In the rectangular supporting surface 39, the cylindrical opening 21 is arranged, through which the optical path 30 falls during the measurement. Furthermore, the slide body 35 comprises a T-handle 40 to make it easy to slide the sample slide 22 into and out of the central cylinder 03.

Figure 4:
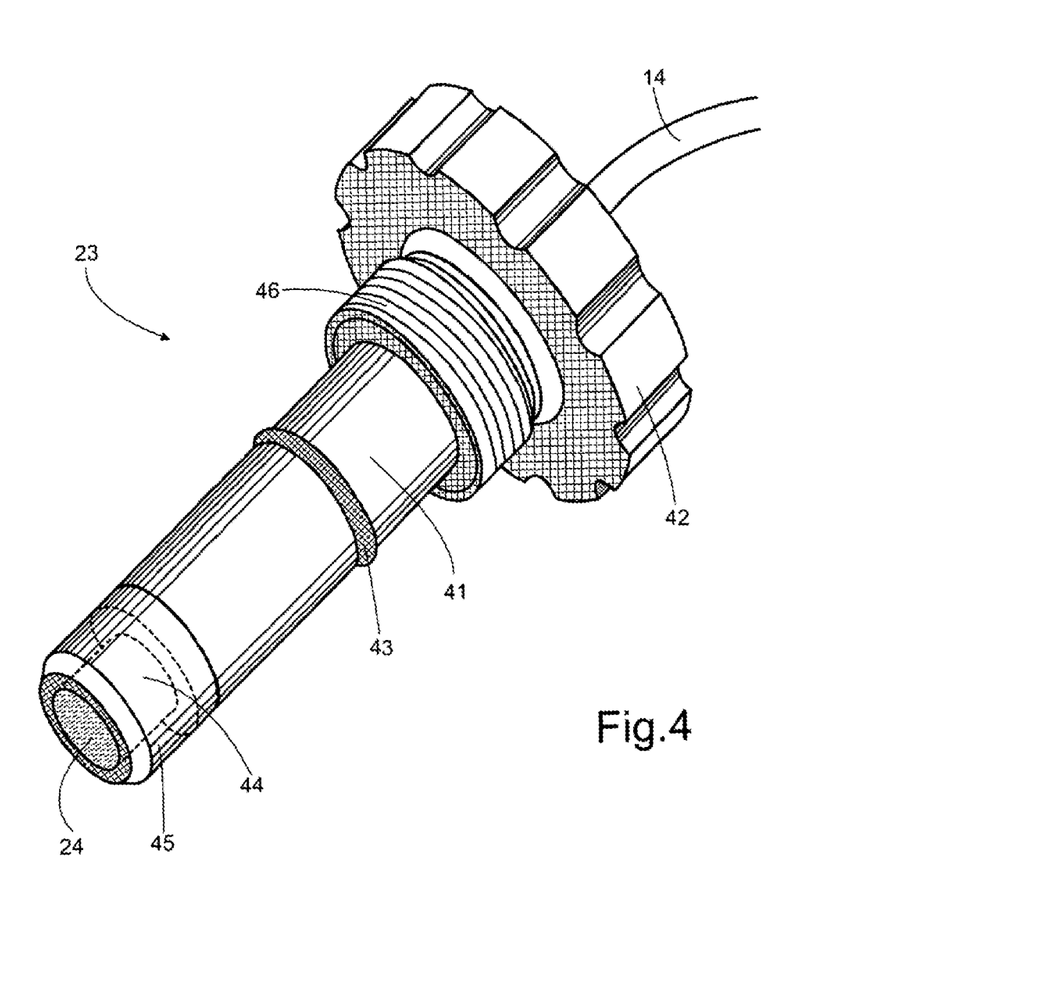
FIG. 4 is a detailed view of an embodiment of the upper lens holder.

FIG. 4 shows the upper lens holder 23 comprising the light-supplying glass fibre 14 in detail. An upper lens holder 41 comprising a hand wheel 42 and a washer 43 which is inserted in a groove can be seen. At the lower end, a mount 44 is screwed in together with the upper collimating lens 24 and secured with a cover cap 45. The upper lens holder 23 is screwed into the central cylinder 03 by means of a thread 46.

Figure 5:
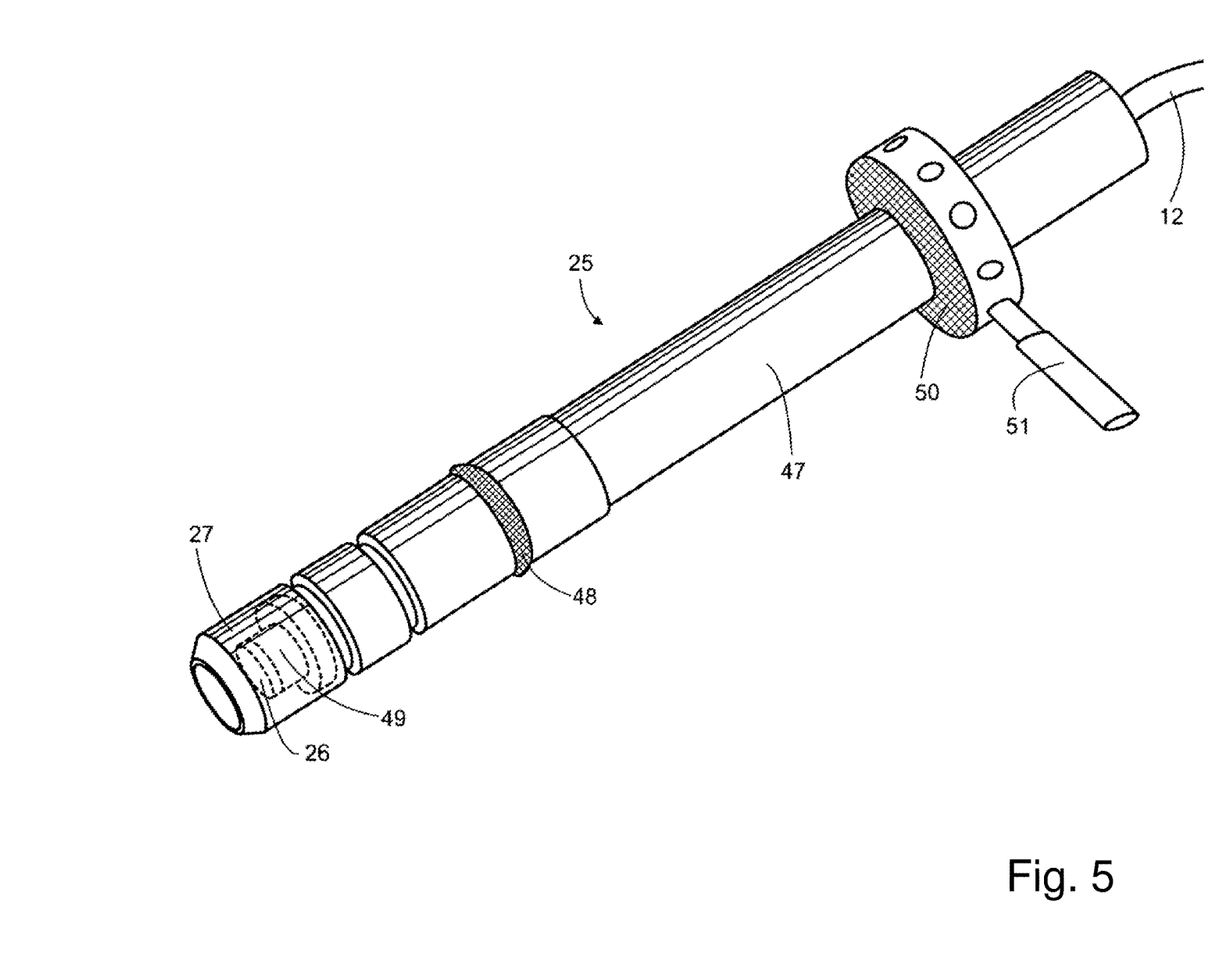
FIG. 5 is a detailed view of an embodiment of the lower lens holder.

FIG. 5 shows the lower lens holder 25 comprising the light-diverting glass fibre 12 in detail. A lower lens holder 47 comprising a sealing ring 48 which is inserted in a groove can be seen. At the upper end, a mount 49 is screwed in together with the lower collimating lens 26 and fixed to the spacer ring 27 by means of a thread. The lower lens holder 25 is simply slid into the central cylinder 03 and holds owing to the sealing ring 48. Furthermore, said holder also comprises an adjusting thread 50, which can be actuated using a handle 51 and is used to focus the lower collimating lens 26. When slid in, the sample slide 20 and the sealing ring 22 are each pressed upwards against the central cylinder 03 by the spacer ring 27, and the sample chamber 04 is thus sealed. Moreover, by means of the spacer ring 27, a minimum distance between the lower collimating lens 26 and the substance sample 05 is maintained, which focuses the optical path 30 on the substance sample 05 in an optimal manner.

Figure 6A:
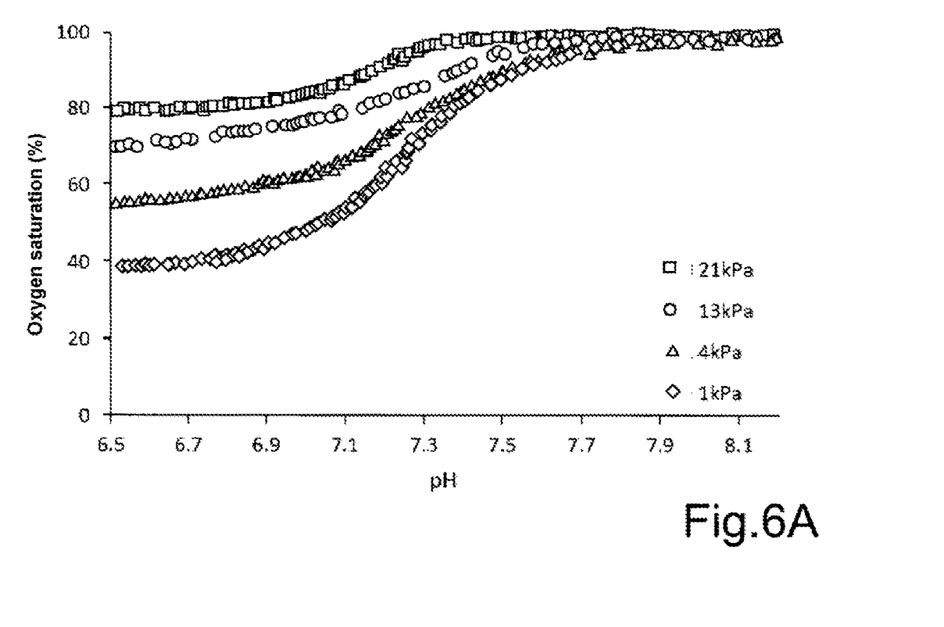
FIG. 6A shows various oxygen-binding curves which have been created with the diffusion chamber according to an embodiment of the invention.

In FIG. 6A, to support the good, achievable resolution of the diffusion chamber 01 according to an embodiment of the invention, various determined oxygen-binding curves of the haemocyanin-containing blood of the Antarctic octopus *Pareledone charcoti* are then shown, measured at a temperature of 0° C. In this case, it is shown that firstly with a total sample volume of only 60 µl (4×15 µl), measurements were able to be carried out at four different oxygen partial pressures from the blood of a single octopus, from which generally only a maximum of 200 µl of blood can be obtained. The high resolution of the binding curves disclosed in this case an asymmetry of the binding curves as a function of the oxygen partial pressure. This phenomenon has hitherto not been detected in previous studies due to a low number of data points and little curve interpolation assuming a symmetrical curve path, and hints at more complex oxygen-binding properties than previously assumed.

Figure 6B:
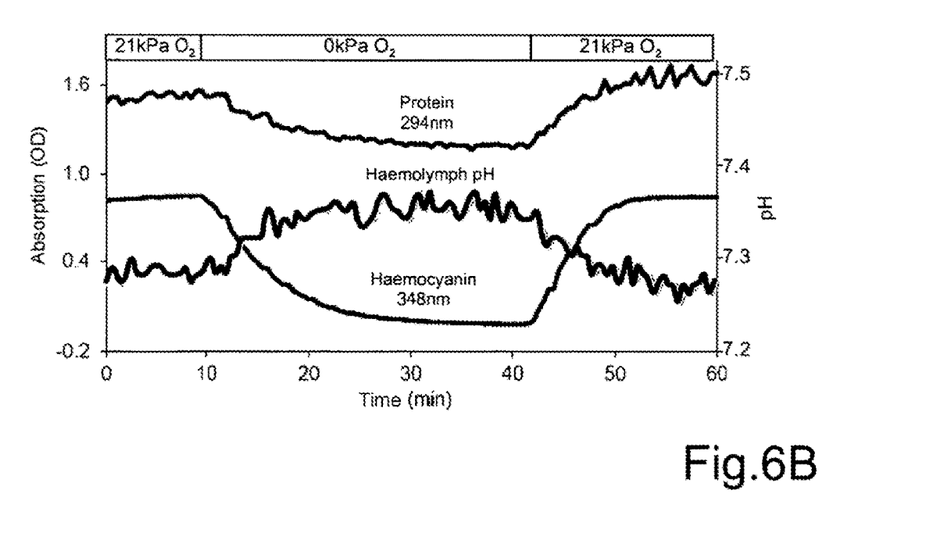
FIG. 6B shows the progression over time of the change in the pH of the blood and of the absorption of a blood sample containing haemocyanin at 294 nm and 348 nm.

The measurements additionally clearly prove in FIG. 6B that the oxygenation and deoxygenation of haemocyanin is associated with a release or intake of carbon dioxide, reflected by the drop or increase in the pH of the analysed blood sample. The broad-spectrum recording additionally disclosed that the maximum protein absorption of cephalopod haeomcyanin is not—as previously assumed—280 nm, but rather 294 nm and there is additionally a dependency between the protein absorption and the degree of oxygenation of the blood pigment. These new findings must be taken into account in the case of future measurements for determining the protein of blood samples.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 diffusion chamber
2 housing
3 central cylinder
4 sample chamber
5 substance sample
6 glass plate
7 optical microsensor (pH optode)
8 syringe body
9 glass fibre
10 plunger
11 needle
12 light-diverting glass fibre
13 spectrophotometer
14 light-supplying glass fibre
15 light source
16 water reservoir
17 gas inlet distributor
18 gas humidifier
19 gas distributor
20 sample slide
21 cylindrical opening
22 sealing ring
23 upper cylindrical lens holder
24 upper collimating lens
25 lower cylindrical lens holder
26 lower collimating lens
27 spacer ring
28 measuring tip
29 edge region
30 optical path
31 inner contour
32 oblique groove
33 angular bend
34 angular bend
35 slide body
36 straight groove
37 oblique hole
38 screw connection
39 supporting surface
40 T-handle
41 upper handle body
42 hand wheel
43 washer
44 mount
45 cover cap
46 thread
47 lower handle body
48 washer
49 mount
50 adjusting thread
51 handle
52 open end of 11

The invention claimed is:

1. A diffusion chamber for determining different parameters of an aqueous substance, the diffusion chamber comprising:
    a vertical central cylinder having at least one sample chamber for receiving a substance sample,
    a needle-shaped pH-measuring sensor having a measuring tip configured to be brought into contact with the substance sample,
    a spectrophotometer having glass-fibre optics configured to penetrate the substance sample, and
    a gas supply into the sample chamber configured to provide a variable gas exposure of the substance sample when determining parameters,
    wherein a sample slide is slid radially into the central cylinder in a gas-tight manner, the central cylinder having a cylindrical opening, above which a cylindrical sealing ring surrounding the sample chamber is disposed on the sample slide,
    wherein a needle of the pH-measuring sensor which is in the form of a syringe-type optical microsensor is inserted into an obliquely extending groove of the sample slide, a glass fibre bearing the measuring tip being movably mounted in the needle, and the needle being guided through the sealing ring in a gas-tight manner, and
    wherein an upper cylindrical lens holder comprising a light-supplying glass fibre and an upper collimating lens is slid axially into the central cylinder in a gas-tight manner above the sample chamber, and a lower cylindrical lens holder comprising a light-diverting glass fibre, a lower collimating lens and a spacer ring is slid axially into the central cylinder in a gas-tight manner below the sample chamber, the sealing ring on the sample slide being pressed against the central cylinder by the inserted spacer ring, the sample chamber being tightly sealed with respect to gases from the surroundings of the diffusion chamber, and a minimum distance being maintained between the lower collimating lens and the substance sample.

2. The diffusion chamber according to claim 1, wherein the needle has two angular bends such that an end of the needle which is open for sliding out the glass fibre is shifted in parallel.

3. The diffusion chamber according to claim 1, wherein an end of the needle which is open for sliding out the glass fibre sits flush with an inner contour of the sealing ring, and wherein the measuring tip of the glass fibre which is slid out of the needle is immersed in an edge region of the substance sample to be studied.

4. The diffusion chamber according to claim 1, wherein the optical microsensor is fixed in the sample slide by an oblique screw connection in a straight groove.

5. The diffusion chamber according to claim 1, wherein the measuring tip has a diameter of 150 μm or less.

6. The diffusion chamber according to claim 5, wherein a measuring volume of 20 μl or less for the substance sample to be studied is inserted in the sample chamber.

7. The diffusion chamber according to claim 1, wherein the optical microsensor has a measurement control for determining at least one measurement per second.

8. The diffusion chamber according to claim 1, wherein the spectrophotometer has a measurement control for determining at least 1000 spectra per second in a continuous wavelength range of between 200 nm and 1100 nm.

9. The diffusion chamber according to claim 1, wherein the spectrophotometer has a halogen or luminescence light source configured to irradiate the substance sample to be studied.

10. The diffusion chamber according to claim 1, wherein the sample chamber is tempered with distilled water or water supplemented with glycol.

11. The diffusion chamber according to claim 1, wherein an adjustable gas mixture is supplied to the sample chamber via the gas supply.

12. The diffusion chamber according to claim 1, wherein additional measuring tips of additional optical microsensors or of chemical microsensors of the substance sample to be studied are introduced into the sample chamber.

13. The diffusion chamber according to claim 1, wherein the substance sample is a substance of biological origin.

* * * * *